United States Patent [19]

Perrut

[11] Patent Number: 4,478,720
[45] Date of Patent: Oct. 23, 1984

[54] FRACTIONATION PROCESS FOR MIXTURES BY ELUTION CHROMATOGRAPHY WITH LIQUID IN SUPERCRITICAL STATE AND INSTALLATION FOR ITS OPERATION

[75] Inventor: Michel Perrut, St Nicolas de Port, France

[73] Assignee: Societe Nationale Elf Aquitaine, Courbevoie, France

[21] Appl. No.: 499,597

[22] Filed: May 31, 1983

[30] Foreign Application Priority Data

Jun. 3, 1982 [FR] France ................................ 82 09649

[51] Int. Cl.$^3$ .......................................... B01D 15/08
[52] U.S. Cl. ...................................... 210/659; 55/67; 55/197; 210/198.2
[58] Field of Search .......................... 55/67, 197, 386; 210/656, 659, 198.2

[56] References Cited

FOREIGN PATENT DOCUMENTS 1673089 1/1971 Fed. Rep. of Germany .
2729462 1/1979 Fed. Rep. of Germany .
1350580 4/1974 United Kingdom .

OTHER PUBLICATIONS

Hardware Adaptations to HPLC Apparatus to Enable Operation as a Supercritical Fluid Chromatograph by McManigill et al. in Hewlett Packard Bulletin 43-59-53-1647, pp. 21-23, 5/1983.
Introduction to Modern Liquid Chromatography by Snyder et al. (Second Edition) pp. 519-522, 1979.
Angewandte Chemie, vol. 19, No. 8, Aug. 1980, pp. 575-587.
Analytical Chemistry, vol. 44, No. 4, Apr. 1972, pp. 681-686.

*Primary Examiner*—John Adee
*Attorney, Agent, or Firm*—Schwartz, Jeffery, Schwaab, Mack, Blumenthal & Koch

[57] ABSTRACT

The present invention concerns a fractionation process of a mixture by elution chromatography.

It is characterized in that the collected eluent is purified, restored to supercritical state and recycled in the head of the column.

It concerns a cracking process of mixtures by elution chromatography with liquid in the supercritical state and an installation for its operation.

14 Claims, 2 Drawing Figures

FRACTIONATION PROCESS FOR MIXTURES BY ELUTION CHROMATOGRAPHY WITH LIQUID IN SUPERCRITICAL STATE AND INSTALLATION FOR ITS OPERATION

The present invention concerns an industrial fractionation process for mixtures, preferably liquid, but also for solid and gaseous by elution chromatography, the eluent used being a liquid in supercritical state.

It is known that a liquid in supercritical state, i.e. in a state chraracterized either by a pressure and a temperature higher than the critical temperature and pressure for a pure body, or by a representative point (pressure, temperature) located beyond the envelope of the critical points represented on a diagram (pressure, temperature) for a mixture, presents, for numerous substances, a solvent power clearly superior to that observed when this liquid is in the gaseous state, even when strongly compressed.

These considerable variations of the solvent power are, furthermore, used in numerous extraction and fractionation process, that, in their operation, belong to liquid-liquid extraction or liquid-solid extraction. One of the advantages of these processes is especially to allow a very easy separation between the solvent (liquid in supercritical state) and the extract, by simple expansion.

This high solvent power has, furthermore, been used for operating analytical methods based on elution chromatography, the eluent being a liquid in supercritical state; in this way, it was possible to fractionate, for analytical purposes, substances having a high molecular weight, that could not be analyzed by chromatography in gaseous phase, and this with analysis times much shorter than those necessary for their analysis by chromatography in liquid phase.

One object of the present invention is to allow, for industrial production, the fractionation of mixtures in their different fractions, by using elution chromatography with, as an eluent, a liquid in supercritical state.

The process according to the invention for the fractionation of a mixture by elution chromatography, the eluent being a liquid in supercritical state circulating continuously at constant flow-rate through the chromatography column is characterized in that is injected periodically at the head of the column, the mixture to be fractionated, the fractions of the mixture being collected, detected at the outlet of the column and each selectively directed towards a separator of a bank of separators in which, by reheating and expansion, the eluent is separated from the constituents of the mixture, the said constituents being collected at the foot of the separators and the eluent as their head, the eluent collected being purified, restored to supercritical state and recycled at the head of the column.

The process is characterized, furthermore, in that the introduction of the fractions of the mixture in the separators is carried out cyclically, according to the periodicity of the injection of the mixture, this periodicity occuring in the form of periodic rectangular impulses.

The present invention also concerns an installation for operating the process cited herein-above, this installation comprising successively a feed pipe of the mixture to be fractionated, an injector, a fractionating column of the mixture by elution chromatography, a detector the output of which is linked up with a bank of traps, each of the inlet pipes in the traps being provided with a heat exchanger, with a control valve and an expansion valve, an eluent recycling module, means for recycling the eluent in the injector, where it is combined with the mixture to be fractionated.

The invention, furthermore, concerns an application of the above mentioned process to the purification of hydrocarbons mixtures and especially of crude naphthalene.

The characteristics and advantages of the present invention will appear more evident from reading through the following discription, given by way of non-limitative illustration with reference to the annexed drawings in which.

Figure 1:
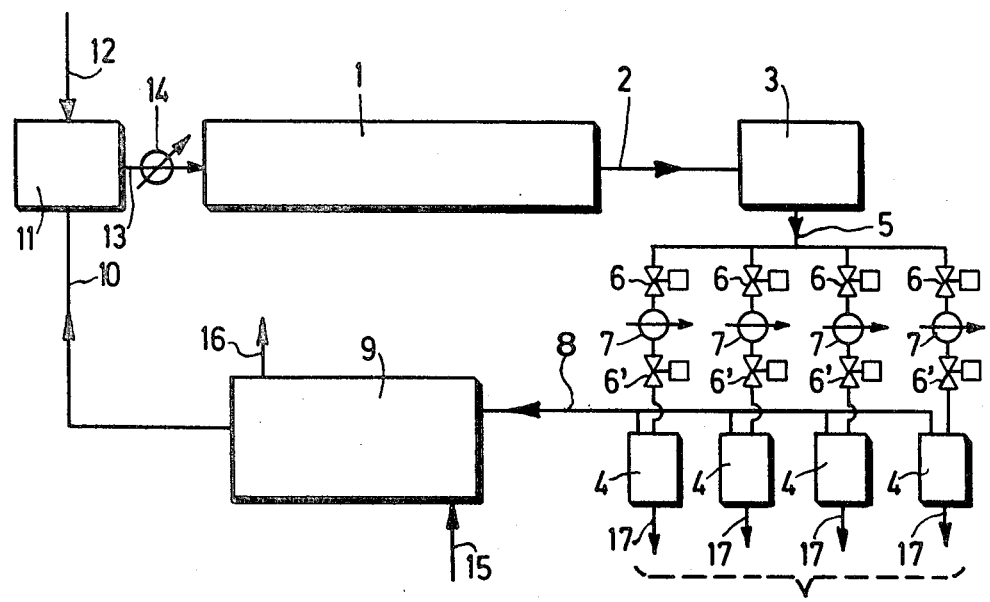
FIG. 1 is a schematic view of a fractionating installation according to the invention.

In the embodiment selected and represented in FIG. 1, a fractionating installation according to the invention comprises, a chromatography column 1, the output of which is connected by a pipe-line 2 to the input of a detector 3, the output of which is linked up by a pipe-line 5 with a bank of traps 4 disposed parallel-wise, the input of each of these traps 4 being provided with a control valve 6, followed by a heat exchanger 7 and an expansion valve 6'. The output of each of these traps is linked up to a purification device to which reference will subsequently be made (not shown in FIG. 1).

A recycling conduit 8 links up at the head traps 4 to an eluent recycling module 9 the output of which is connected by a pipe-line 10 to an injector 11 that comprises an input 12 for the mixture to be fractionated and an output connected by a pipe-line 13, through a heat exchanger 14, at the input of column 1.

Recycling module 9 comprises furthermore an input 15 for controled eluent feed and a drain outlet 16.

Means, not shown, ensure the cyclic opening and closing of valves 6 in function of the periodicity of the injection of mixture in 12 and the indications supplied by detector 3.

In the installation represented, for operating the process according to the invention, the eluent in the supercritical state issuing from the recycling module 9, sweeps continuously, at a constant flow-rate, the chromatography column 1, after having received in injector 11, injections of the mixture from input 12 to be fractionated, generally in the liquid form.

For a better dispersion of the mixture throughout the eluent a static mixer at the level of injector 11 is advantageously provided. The temperature of the fluid (eluent plus mixture) is adjusted to the desired value by means of heat exchanger 14, then this fluid is introduced into column 1 maintained in an adiabatic state.

Preferably, the chromatography column is constituted by a cylindrical tube filled with a granular coating formed either by an adsorbent porous solid presenting a selective behavior with respect to constituents of the mixture to be separated, or by an inert porous solid that was previously impregnated with a liquid having a high molecular mass also having a selective behavior with respect to the mixture to be separated.

According to the principle of elution chromatography the different constituents of the mixture will be displaced at different speeds within the column due to their affinity difference with the stationary phase (adsorbent or impregnated phase).

Consequently, at the output of the column, it is possible to obtain separated "peaks" of each of the constituents during the time of operation, as can be observed from the indications supplied by detector 3. The nature of this latter depends on the products used: spectrophotometer, flame ionisation, catharometer, measurement of the dielectric constancy.

Thus, it is possible to realize the injection of the mixture to be fractionated in the form of rectangular impulses during a time $t_1$, with a periodicity or cycle time tc. (FIG. 2a, giving the flow-rate of mixture D as a function of function of time t).

Figure 2:
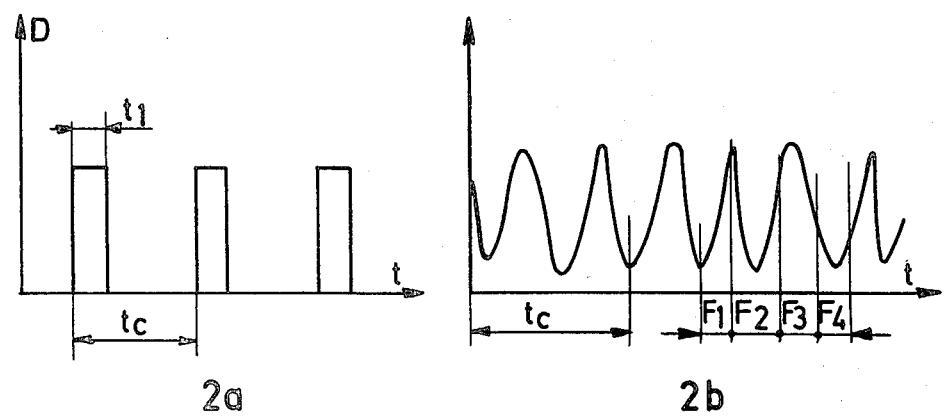
FIG. 2a is a diagram giving in ordinates the flow-rate of the mixture to be fractionated and in abscissa the time.
FIG. 2b is a diagram corresponding to the previous one and giving, in function of time, the signal detected at the output of the chromatography column, the "peaks" of the different fractions of the initial mixture.

At the output of the column, are shown "peaks" corresponding to each of the constituents, with the same periodicity tc, these peaks characterized the different fractions of the mixture, $F_1$, $F_2$ . . . (FIG. 2b).

These fractions are very simply selectively collected in traps 4 by a cyclic motion of the valves 6 actuating the input of these valves under the control of the indications of the detector 3, with periodicity tc.

Traps 4 are advantageously simple gas-liquid separators. Indeed, the separation of the eluent and the initial fractions of the mixtures thus collected is extremely simple; it is sufficient to carry out a slight heating in heat exchangers 7 and a simple expansion in valves 6' so that the liquid in supercritical state is either brought to a state in which its volumic mass is much smaller than previously and that thus the solubility of the fractions of the initial mixture are largely decreased. The eluent thus issues at the head of banks 4 through pipe-line 8 by carrying only small quantities of products, the major part of said products being evacuated at the foot of the traps in 17.

The eluent issuing at the heads of traps 4 and which in the gaseous state, must be reconditioned before being recycled in the supercritical state or as a subcritical liquid with a purity compatible with its reutilisation as an eluent for a fresh cycle.

It still contains a small part of the components of the mixture and it must thus be purified if it is desired to recycle it in order to reduce the eluent consumption and thus operating costs. To do this, it is possible to use in numerous applications an adsorbent bed that will selectively capture the impurities contained in the liquid (active coal, molecular sieve, etc. . . . ); several adsorbent beds will be classically used, at least one of which will be used at every instant in order to purify the eluent while the others will be in regeneration stage according to the procedure normally used with this type of apparatus. The purified gas can thus be treated in two different manners prior to recycling:

either compressed in the gaseous state at the pressure desired for the recycling and cooled in a heat exchanger to the temperature desired for the recycling;

or condensed in the liquid state at the output pressure of the adsorbent bed, compressed by a pump at the pressure desired then slightly heated prior to injection 11 or simply after injection in heat exchanger 14 in order to obtain at the input of the column 1 the pressure and temperature desired.

In certain applications, it is possible to include in the recycling module 9 drying bed (molecular sieve, for example) if the chromatography column and/or mixture to be separated is in danger of being altered by the presence of water in the eluent; if the eluent is a fuel it can be necessary to include a catalytic deoxygenation reactor in order to eliminate all trace of oxygen in the eluent recycled by combustion with the eluent. The drying bed and the catalytic deoxygenation reactor will be preferably disposed after the compressor or the recycling module pump. If both are necessary, the drying bed will always be downstream of the deoxygenation reactor.

In the majority of applications, it will be necessary to buffer tanks for the gas issuing from the traps of compressed gas or subcritical liquid after compression in order to allow a correct control of the flowrate of the eluent.

In order to eliminate the accumulation of inert substances present in the starting circuit and injected with the mixture, a small flow-rate in 16 is continuously drained while maintaining the quantity of eluent present in the circuit by a controlled eluent feed in 15.

By way of example, the input temperature of the mixture in the column can be advantageously selected between Tc and 1.2 Tc if Tc is the critical temperature of the eluent (and even in many cases between Tc and 1.05 Tc); the input pressure of the mixture must be superior to critical pressure Pc of the eluent and may be advantageously fixed between 1.05 Pc and 2 Pc (and in certain particular cases it can reach 3 Pc.); the pressure in the traps is on the other hand lower than the critical pressure Pc of the eluent and may be selected between 0.5 and 0.95 Pc and advantageously between 0.8 and 0.9 Pc in order to limit the cost of recompression without too much reducing the trapping yield.

The determinant advantages of this process are immediately understood in comparison to preparative chromatography processes in gaseous phase and liquid phase:

the temperature used for the fractionation can be very much lower than in chromatography in gaseous phase due to the high solubility of the components of the mixture in the liquid in supercritical state and due to the fact that the mixture does not have to be vaporized; the major obstacles inherent in the fragility of the molecules and the stability of the stationary phases (about all polar phases) are thus overcome;

the eluent-fraction separation is much easier than in gaseous phase chromatography (condensation on a cold wall with the problem of fog formation) and than in liquid phase chromatography (distillation of mixtures highly diluted by the eluent).

Other advantages can also be cited, relative to the economy of the operation, bound to the low viscosity of the liquid in supercritical state and its large diffusivity allowing use of high passage speeds without affecting the separation efficiency and thus leading to high productivities.

In the case where the mixture to be crocked is initially in the solid or gaseous form, it is advantageous to dissolve it beforehand in a certain volume of eluent (in the liquid or supercritical state according to the case) and to use in the process described this solution in the same way as liquid mixtures.

In certain applications, it can be advantageous to cause the input pressure of the eluent of the column to vary with a period equal to that of the injection cycle; an increase of the pressure during the cycle can reduce passage time of the most retained compounds and thus increase the productivity of the installation.

Examples of application of the process are given herein-under.

EXAMPLE 1

The chromatography column, that is 1.5 m long with a 0.125 m internal diameter, is packed with a classic material (ground chromosorb b type baked brick having a granulometry of 200–250μ) impregnated with glycol polyethylene (average molecular weight 6000) at a rate of about 20%; the vector liquid used is n-pentane (critical coordinates Tc=469.70K and Pc=3.33 MPa).

The input temperature in the column is very carefully maintained at 215° C. (about ±0.3° C.) and the input pressure at 4.20 MPa (±0.02 MPa); the liquid flow-rate is controlled with precision at 100 Kg/h. The traps are maintained at a pressure of 2.2 MPa and at a temperature of 210° C.

Under these conditions, the purification of naphthalene

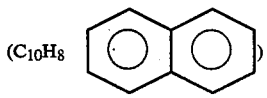

will be affected; a classic measurement of the number of theoretical plates carried out by injection of pure naphthalene leads to 450 (±50), i.e. a theoretical stage height close to 3 mm; this efficiency can only be obtained due to a very careful tamping of the column that is subjected at the time of filling to a cycle of violent vibrations and shocks, and to a very careful adjustment of operating parameters.

The crude naphthalene to be purified contains about 5% impurities constituted by alkylated monocyclic hydrocarbons

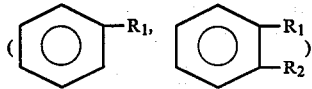

and alkylated dicyclic hydrocarbons

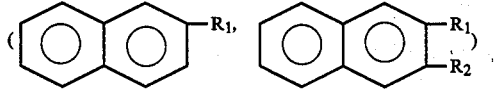

as well as traces of hydrocarbons having various structures, the boiling points of which are close to that of naphthalene (the purity of crude naphthalene can be evaluated by its melting point, i.e. Tf=76.8° C.).

For injection lasting 15 s and corresponding to 60 g for a flow-rate of 4 g/s, the optimal parameters of the injection and trapping cycle are selected by way of example:
injection: 0–15 s;
pure product trap: 190–220 s;
product trap to be recycled: 180–190 s and 220–235 s;
concentrated impurities trap: 0–180 s and 235–290 s.

A yield of 70% in "pure" product (about 0.5% impurities melting temperature Tf=79.6° C.), 20% product to be recycled (Tf=77.2° C.) and 10% concentrated impurities is obtained.

Taking into account the passage time of the least retained compound (about 150 s) and in order to increase productivity, the time of the cycle can be reduced to 140 s by carrying out the injection prior to the exit of the previous "peak" from the column, i.e. t=150 s in the previous cycle, this gives the following cycle:
injection: 0–15 s;
pure product trap: 40–70 s;
product trap to be recycled: 30–40 and 70–85 s;
impurities trap: 0–30 and 85–140 s.

The results obtained for the yields and purities remain close to those described herein-above, the productivity with this cycle reaches 1.05 kg/h of the purified product.

In this application, the purification of the vector liquid is effected on an active carbon bed having a capacity of about 100 l. As a precaution regeneration took place approximately every 5 days; the pentane and the load containing infinitesimal quantities of water, it was not necessary to operate a dehydratation treatment.

EXAMPLE 2

The same product to be purified as before was treated.

The chromatography column that was 0.4 m long with a diameter of 0.125 m is filled with grafted silica (RP18 type linear carbonated chains with 18 carbons) with an average granulometry of 10 μm; the vector fluid used in carbon dioxide (critical coordinates: Tc=304.30 K and Pc=7.38 MPa).

The input temperature in the column is carefully maintained at 35° C. (±0.1° C.) and the input pressure at 15 MPa (±0.05 MPa); the eluent flow-rate is adjusted with precision to 115 kg/h. The traps are maintained at a pressure of 6 MPa and a temperature of 80° C.

A classic measurement of the number of theoretical plates carried out under these conditions by injection obtained a result of close to 0.16 mm; this efficiency can only be obtained due to a very careful preparation of the column with shocks, vibrations and compression of the filling and a very precise adjustment of operating parameters.

For an injection of 20 s and corresponding to 50 g for a flow-rate of 2.5 g/s, optimal parameters of the injection and trapping cycle have been selected by way of example:
injection: 0–20 s;
pure product trap: 280–310 s;
product trap to be recycled: 270–280 s and 310–325 s;
concentrated impurities trap: 0–270 and 325–375.

A yield of 75% "pure product" (about 0.4% impurities, melting point Tf=79.7° C.), 14% product to be recycled (Tf=77° C.) and 11% concentrated impurities are obtained.

As in the previous case, the productivity of the unit can be increased by carrying out the injection prior to the output of the preceding "peak" of the column, i.e. t=115 s in the preceding cycle, this gives the following cycle:
injection: 0–20 s;
pure product trap: 20–50 s;
product trap to be recycled: 10–20 s and 50–65 s;
impurities trap: 0–10 s and 65–115 s;
i.e. a productivity equal to about 1.15 kg/h of pure product.

In this application, the purification of the vector liquid was operated under conditions identical to those of the previous example.

I claim:

1. A process for fractionating a mixture by supercritical fluid elution chromatography, said process comprising the steps of:
   (a) continuously feeding an eluent fluid in the supercritical state at a constant flow rate through an elution chromatography column;
   (b) periodically injecting an amount of a mixture to be fractionated into the supercritical eluent fluid at the head of the elution chromatography column;
   (c) detecting the emergence of fractions of said mixture in the supercritical eluent stream emerging from the elution chromatography column;
   (d) selectively directing portions of said supercritical eluent stream containing detected fractions of said mixture to individual separators of a bank of parallel separators;
   (e) separating mixture components from each eluent portion by allowing the supercritical eluent of each portion to expand in the separator to which it was directed;
   (f) withdrawing separated mixture components from the bottom of each separator;
   (g) withdrawing gaseous eluent from the top of each separator;
   (h) purifying the withdrawn eluent;
   restoring the purified eluent to the supercritical state, and
   (j) recycling the supercritical eluent from step (i) to step (a) such that the quantity of eluent present in the circuit of steps (a) through (j) is maintained constant.

2. A process according to claim 1, wherein the selective direction of the mixture fraction/containing eluent portions to the separators is carried out cyclically according to a cycle corresponding in periodicity to the periodicity of the injection of the mixture into the eluent at the head of the column.

3. A process according to claim 1, wherein accumulation of impurities in the eluent is limited by continuously withdrawing a minor portion of eluent from the circuit and replacing the withdrawn eluent with an equal amount of fresh eluent to maintain a constant quantity of eluent present in the circuit.

4. A process according to claim 1, wherein the supercritical eluent is fed to said elution chromatography column at a temperature between the critical temperature and 1.2 times the critical temperature of the eluent and at a pressure between 1.05 times the critical pressure and 3 times the critical pressure of the eluent.

5. A process according to claim 4, wherein the eluent is fed to the elution chromatography column at a temperature between the critical temperature and 1.05 times the critical temperature and at a pressure between 1.05 times the critical pressure and 2 times the critical pressure.

6. A process according to claim 1, wherein the pressure in the separators is between 0.5 $P_c$ and 0.95 $P_c$ where $P_c$ represents the critical pressure of the eluent.

7. A process according to claim 6, wherein the pressure in the separators is between 0.8 $P_c$ and 0.9 $P_c$ where $P_c$ represents the critical pressure of the eluent.

8. A process according to claim 1, wherein the purified eluent is restored to the supercritical state by compressing the eluent.

9. A process according to claim 1, wherein the purified eluent is restored to the desired supercritical state by successively condensing and then compressing it.

10. A process according to claim 1, wherein the temperature of the purified eluent is adjusted by heat exchange in order to be recycled at the desired supercritical conditions.

11. A process according to claim 1, wherein the pressure at which the supercritical eluent is fed to the elution chromatography column is modulated as a function of time, said function having a periodicity identical to the periodicity of the injection cycle.

12. A process according to claim 1, wherein the mixture to be fractionated comprises a hydrocarbon mixture.

13. A process according to claim 12, wherein said hydrocarbon mixture comprises crude naphthalene.

14. Apparatus for fractionating a mixture by supercritical fluid elution chromatography, said apparatus comprising:
   (a) an elution chromatography column;
   (b) means for continuously feeding an eluent fluid in the supercritical state at a constant flow rate through said elution chromatography column;
   (c) means for periodically injecting an amount of a mixture to be fractionated into the supercritical eluent fluid at the head of said elution chromatography column;
   (d) means for detecting the emergence of fractions of said mixture in the supercritical eluent stream emerging from the elution chromatography column;
   (e) a bank of parallel separators selectively connectable to said detecting means;
   (f) means for selectively directing portions of said supercritical eluent stream containing detected fractions of said mixture to individual separators of said bank of said parallel separators;
   (g) means for allowing supercritical eluent to expand in said separators;
   (h) means for withdrawing separated mixture components from the bottom of each separator;
   (i) means for withdrawing gaseous eluent from the top of each separator;
   (j) means for purifying the withdrawn eluent;
   (k) means for restoring the purified eluent to the supercritical state, and
   (l) means for recycling the supercritical eluent from the purification means to the supercritical eluent feeding means.

* * * * *